United States Patent [19]

Bisera et al.

[11] Patent Number: 4,530,696
[45] Date of Patent: Jul. 23, 1985

[54] MONITOR FOR INTRAVENOUS INJECTION SYSTEM FOR DETECTING OCCLUSION AND/OR INFILTRATION

[75] Inventors: Jose Bisera, Camarillo; Max H. Weil, Beverly Hills, both of Calif.

[73] Assignee: Institute of Critical Care Medicine, Los Angeles, Calif.

[21] Appl. No.: 503,410

[22] Filed: Jun. 13, 1983

[51] Int. Cl.³ .............................................. A61M 5/20
[52] U.S. Cl. ................................... 604/253; 604/67; 128/DIG. 13
[58] Field of Search ............................. 128/DIG. 13; 604/65–67, 153, 253, 50, 245, 246

[56] References Cited

U.S. PATENT DOCUMENTS

| | | | |
|---|---|---|---|
| 3,985,133 | 10/1976 | Jenkins et al. | 604/67 |
| 4,111,198 | 9/1978 | Marx et al. | 128/DIG. 13 X |
| 4,137,913 | 2/1979 | Georgi | 128/DIG. 13 X |
| 4,187,057 | 2/1980 | Xanthopoulos | 604/153 X |
| 4,213,454 | 7/1980 | Shim | 604/65 |
| 4,345,594 | 8/1982 | Bisern et al. | 604/67 X |
| 4,392,847 | 7/1983 | Whitney et al. | 128/DIG. 13 X |
| 4,394,862 | 7/1983 | Shim | 604/67 |

Primary Examiner—Edward M. Coven
Attorney, Agent, or Firm—Freilich, Hornbaker, Rosen & Fernandez

[57] ABSTRACT

A monitor is described for use with an intravenous injection system of the type that includes an accumulator (18) located between the pump (14) and the needle (28) that connects to the patient's vein. The monitor generates an alarm when there is infiltration (no resistance to outflow, as when the needle withdraws from a vein) or occlusion (the needle is blocked). The monitor includes a pressure sensor (32) coupled to the accumulator, and a circuit (34) which responds to the rate of change of the pressure to operate an alarm when the rate of change exceeds a predetermined amount such as 5 mm Hg, but only when it exceeds that value over a particular time period such as 10 seconds or one minute.

6 Claims, 3 Drawing Figures

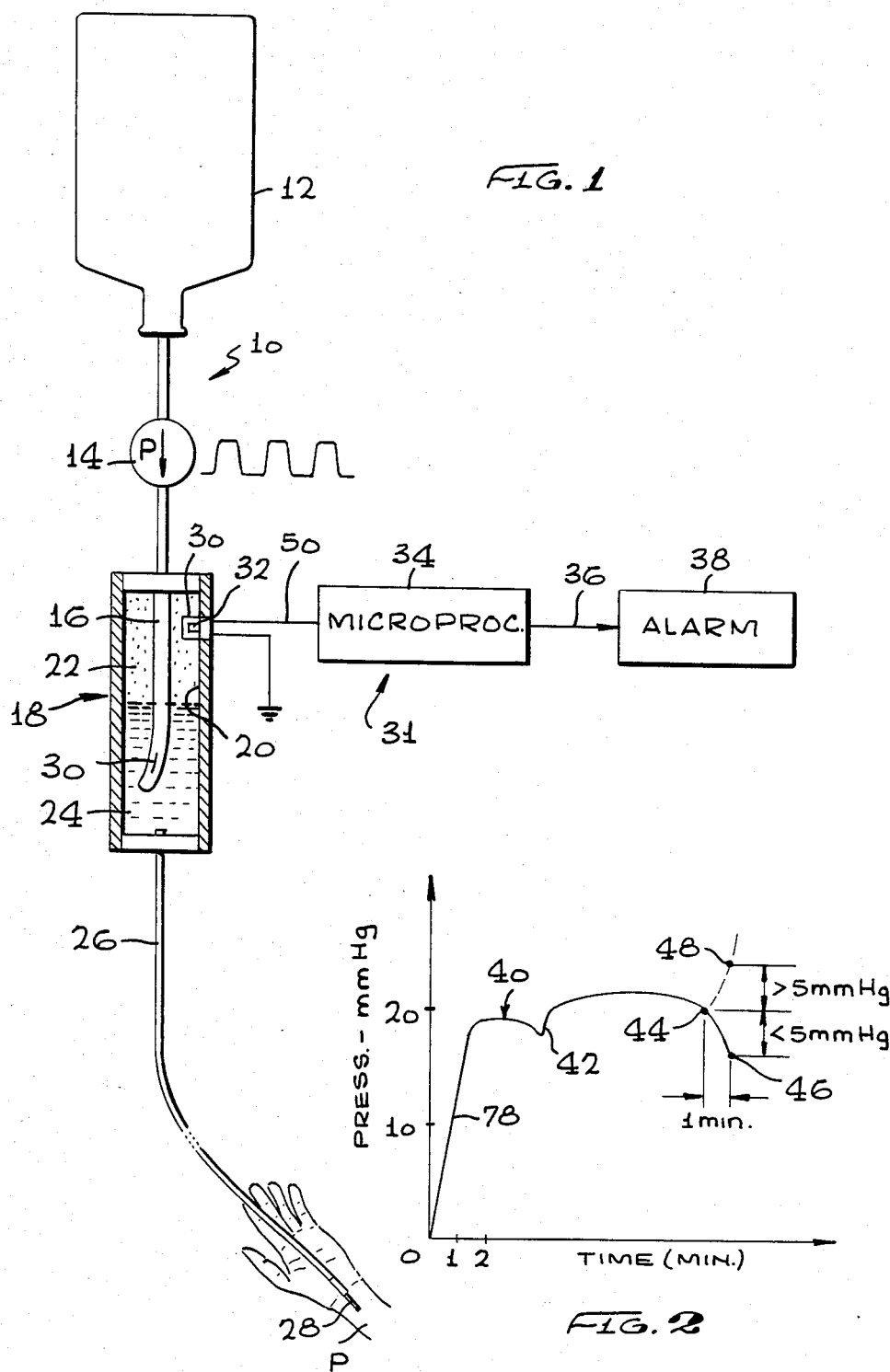

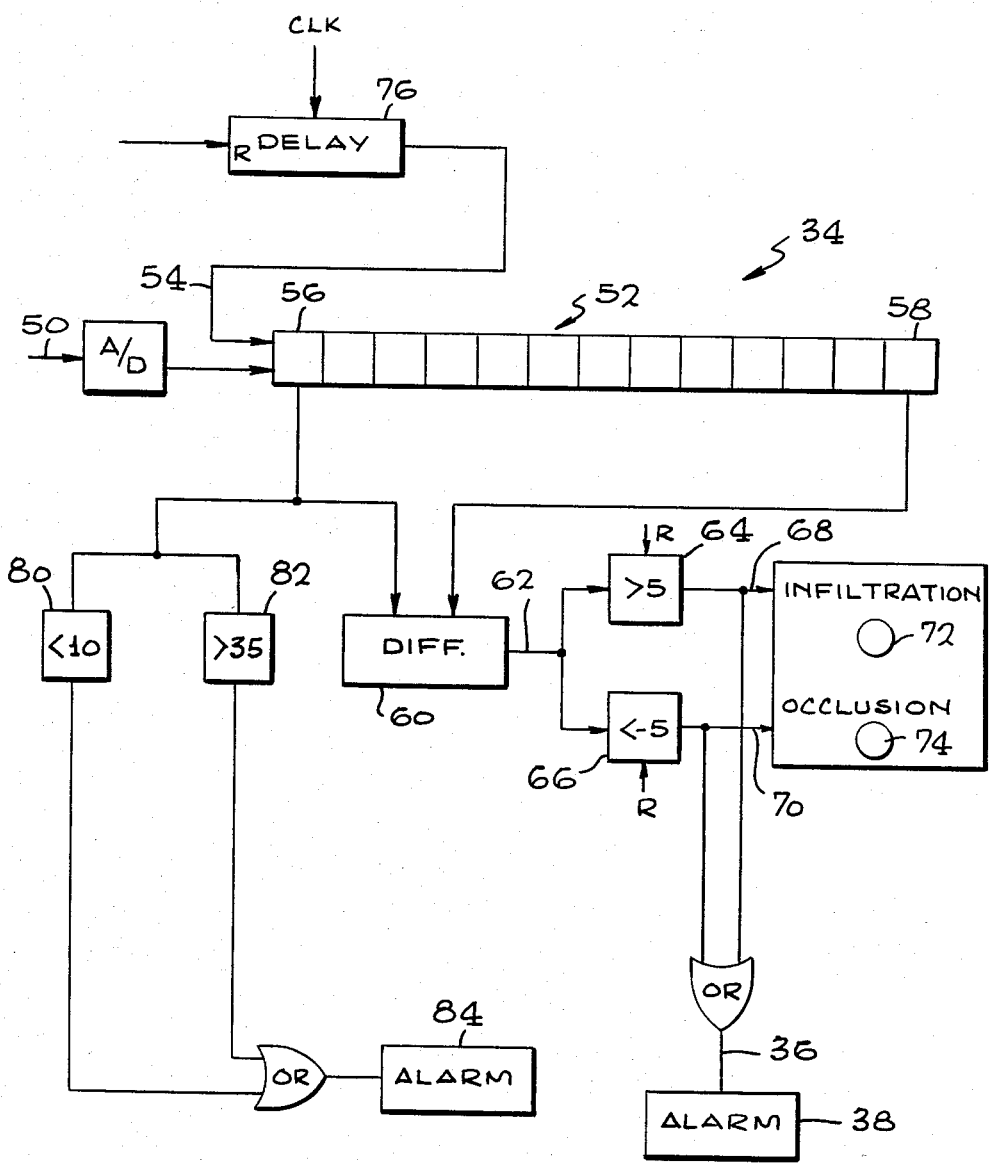

MONITOR FOR INTRAVENOUS INJECTION SYSTEM FOR DETECTING OCCLUSION AND/OR INFILTRATION

BACKGROUND OF THE INVENTION

A low cost intravenous injection system can include a peristaltic pump which pumps a quantity of intravenous fluid in pulses, such as every time a tube is compressed. The fluid pulses are applied to a pressure moderator which smooths the pressure, and is applied from the pressure moderator to a needle or the like that is connected to a patient's vein. A system of this type is described in U.S. Pat. No. 4,345,594 by Bisera et al. Two types of problems that can arise in intravenous injection, are infiltration and occlusion. In infiltration, fluid passes out of the needle with very low resistance. This can occur when the tip of the needle has withdrawn from the vein and is pumping fluid into an area surrounding the vein where it does not experience the moderate backpressure that would be normally encountered in a vein. In occlusion, there is greater than expected resistance to the outflow of fluid from the needle, as where the tip of the needle is blocked by tissue. A simple system for monitoring the injection system to guard against infiltration or occlusion, would add to the usefulness of simple injection systems.

SUMMARY OF THE INVENTION

In accordance with one embodiment of the present invention, a monitor is provided for detecting improper flow of fluid pumped by an intravenous injection system. The monitor includes a pressure sensor coupled to an accumulator and a circuit which is responsive to the rate of change of pressure, to generate an alarm signal upon the rate of change of pressure exceeding a predetermined value. However, the circuit generates an alarm signal only if the rate of change exceeds that value over a predetermined length of time.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partially sectional elevation view of an intravenous injection system constructed in accordance with the present invention.

FIG. 2 is a graph showing an example of variation of pressure with time at a location in the system of FIG. 1.

FIG. 3 is a block diagram of a portion of the system of FIG. 1.

DESCRIPTION OF THE PREFERRED EMBODIMENT

FIG. 1 illustrates an intravenous injection system 10 which includes a container 12 that holds a fluid to be administered such as a saline solution. A peristaltic pump 14, such as of the type described in U.S. Pat. No. 4,345,594 pumps the fluid through a check valve 16 into an accumulator or pressure moderator 18. The pressure moderator has a storage area 20 which includes a gas-containing region 22 above a liquid-containing region 24. The intravenous liquid passes from the moderator 18 through a catheter 26 to a needle 28 that is inserted into a vein of a patient P. The moderator 18 and catheter 26 form a conduit that couples the pump 14 to the needle.

The moderator tube 16 is formed of a resilient tube with a lower end that is closed and that has a slit 30. At every pulse of the peristaltic pump 14, a pulse of liquid passes out of the slit 30 to fill the bottom area 24 of the moderator chamber. As the level of liquid rises in the storage area 20, the pressure of gas in the upper area 22 increases, so that liquid is applied at a progressively higher pressure to the catheter 26. As the pressure increases, fluid flows at an increasing rate into the catheter, until the rate of inflow and outflow to the moderator is equal. Under normal operating conditions, when the needle 28 at the end of the catheter is subjected to a moderate backpressure which is in the range typically encountered in veins of patients, the pressure in the moderator chamber 20 will be such that there is always a moderate level of liquid in the chamber. The level of the liquid will be slightly higher or lower depending upon whether the backpressure is slightly higher or lower. However, if there is infiltration or occlusion, where the backpressure experienced at the needle suddenly decreases or increases beyond the expected range, then this may indicate that the needle is not positioned properly. Medical personnel should be notified of this, not only to assure continued application of fluid to the patient, but to notify them that the needle may cause harm to the patient.

In accordance with the present invention, infiltration and/or occlusion is monitored by a system 31 which includes a sensor 32 that senses the pressure in the chamber or storage area of the moderator. The sensor is coupled to the gas-containing area 22 through a bacterial filter to isolate it from pulses of liquid flow, and to maintain sterility of the moderator chamber 20. The sensor 32 is connected to a circuit 34 that senses whether the pressure in the chamber or storage area 20 of the pressure moderator has increased or decreased at more than a predetermined rate, over a particular period such as one minute. In the event of such an increase or decrease, the circuit delivers a signal over line 36 to an alarm 38 which may be an audible or other type, to alert medical personnel that there may be an infiltration or occlusion.

The variation of pressure with time in the storage area 20 is indicated by a graph 40 in FIG. 2. During an initial period when the system is started and fluid starts to fill up the pressure moderator, the pressure therein gradually increases over a period such as two minutes, until it reaches a largely constant level, such as 20 mm Hg (millimeters of mercury). Thereafter, small perturbations may be encountered, as where a patient moves and changes the backpressure on the needle, or where the height of the location on the patient where the needle is connected is altered. These changes are typically relatively small sudden changes such as indicated at 42, or are relatively gradual changes. However, when infiltration occurs, as where a needle is dislodged from the vein of the patient and is lodged in the surrounding tissue, then a more rapid change in pressure will be encountered. In the graph, the point 44 represents a time when a needle has pulled out of a patient's vein and the pressure begins to drop. In this case, the pressure will decrease at a considerable rate, and this decrease will continue for an extended period. In a similar manner, the pressure will increase if there is accumulation of fluid in the tissues, or if there is occlusion of the needle—catheter system.

The circuit 34 is constructed to avoid false alarms when the pressure in the moderator chamber 20 changes in a manner that does not indicate infiltration or occlusion. That is, where the rate of change is rapid but continues for only a short period, or the total pressure change is considerable but very gradual, the circuit does not generate an alarm. Instead, the circuit is constructed primarily to generate an alarm only if there is a rapid change over an extended period. In FIG. 2, where the expected pressure is about 20 mm Hg, a change of more than 5 mm Hg during an extended period such as one minute, may be considered an indication of infiltration or occlusion. In that case, the pressure at 44 would change after one minute to a pressure indicated at 46 or 48 which respectively indicates infiltration or occlusion.

FIG. 3 illustrates details of one example of circuitry which can be used for the circuit 34 of FIG. 1. The circuit includes an input line 50 connected to the pressure sensor, and which carries signals representing the pressure in the upper part of the pressure moderator. The digital equivalent of this pressure is entered into a serial shift register 52. The register also receives a divided clock signal over line 54, so that at intervals such as every five seconds, a new value is entered into the first portion or cell 56 of the register and all values are shifted therein. After a predetermined time such as one minute, the information originally in the beginning cell 56 reaches the last portion or cell 58 of the register. A difference circuit 60 which is connected to the first and last cells of the register, generates a signal on line 62 representing the value in register cell 56 minus the value in register cell 58. The signal on line 62 is delivered to two other circuits 64, 66. The circuit 64 generates an output signal on line 68 if the difference on line 62 is greater than 5, which indicates that the pressure has fallen by more than 5 mm Hg in a one minute period, to thereby indicate that there is infiltration. The other circuit 66 generates a signal on its output line 70 if the change in pressure is less than minus 5, which indicates there is occlusion. Either of these conditions can be indicated by the lighting of lamps 72, 74. In addition, signals on line 68 or 70 can be used to operate the alarm 38, which may be an audible alarm that calls medical personnel.

When the system is first started and the pump 14 begins to fill the pressure moderator, the pressure rises for a period such as two minutes, as indicated at 78 in FIG. 2. A delay circuit 76 then delays the delivery of clock pulses to the shift register 52. At startup, various elements of the circuit are reset or deactivated for a limited period.

Thus, in the circuit 34, an alarm is given if the pressure changes at more than a predetermined rate such as 5 mm Hg per minute, and if this rate continues for a predetermined period. The period should be more than several seconds, or in other words more than 10 seconds, to avoid false alarms arising from perturbations such as mentioned earlier. While the two pressure values that are compared occur at times spaced apart by perhaps one minute, the rate of change is checked at more frequent intervals such as every five seconds, to minimize the delay before an alarm is given after the rate for the minimum period is exceeded.

The circuit 34 also includes a pair of subcircuits 80, 82 that detect whether the absolute pressure level has fallen below 10 mm Hg or risen above 35 mm Hg, to sound another alarm 84. The circuit 34 can be implemented by a micro-processor or computer.

Thus, the invention provides a monitor for use with an intravenous injection system, which indicates the possibility of infiltration and/or occlusion. The monitor system detects the pressure in the chamber of a pressure moderator and stores a signal representing that pressure. After a predetermined period such as one minute, the circuit compares the previously stored signal representing previous pressure to a newly received signal representing current pressure. If the absolute value of the difference is greater than a predetermined threshold level, then the circuit generates an alarm signal. In this way, a monitor generates an alarm signal if the rate of change exceeds a predetermined amount, only if it exceeds this amount during a predetermined period which is great enough to avoid common small sudden changes in pressure that do not indicate a situation requiring the attention of medical personnel.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. In an intravenous injection system of the type that includes a pump which applies intravenous fluid to a pressure moderator, wherein the pressure moderator has a storage area including a gas-containing region above an intravenous fluid-holding region, and that also includes an outlet from said fluid-holding region for application through a needle or the like to a vein of a patient, the improvement of a monitor for detecting improper patient inflow including infiltration and/or occlusion, comprising:

a pressure sensor coupled to said storage area for sensing the pressure therein;

alarm means operable to generate an alarm signal indicating improper fluid flow; and circuit means coupled to said pressure sensor and said alarm means, said circuit means responsive to the rate of change of pressure sensed by said pressure sensor, for operating said alarm means to generate an alarm signal upon the rate of change of said pressure exceeding a predetermined value over a predetermined period of time of more than 10 seconds.

2. The improvement described in claim 1 wherein:

said circuit means is constructed to operate said alarm means upon a change of pressure in said storage area of about 5 millimeter mercury in a period of about one minute.

3. The improvement described in claim 1 wherein:

said circuit means includes a register for storing a signal representing pressure, and a comparing circuit for comparing a recently-received signal representing recent pressure, to a previously-received signal stored a predetermined period in said register, whereby a large rate of change for only a brief period does not cause operation of the alarm means.

4. The improvement described in claim 1 wherein:

said pressure sensor is coupled to said gas-containing region of said accumulator.

5. An intravenous injection system which can detect infiltration and/or occlusion in a needle or the like through which fluid is to be administered to a patient comprising:

a pump for pumping intravenous liquid;
   needle means for applying liquid to a patient;

a conduit which couples said pump to said needle means;

a pressure sensor coupled to said conduit to measure the pressure therein;

a circuit coupled to said sensor for receiving and storing signals representing a pressure sensed by said sensor, for comparing a recently received signal with a previous signal that was received more than 10 seconds prior to receipt of the recently received signal, and for generating an alarm indication when the difference between the compared signals exceeds a predetermined value.

6. A method for monitoring an intravenous injection system of the type which includes a conduit located between a pump and a needle or the like which connects to a patient's vein, to detect infiltration and/or occlusion, comprising:

sensing pressure in said conduit and generating signals representing the sensed pressure;

storing said pressure-indicating signals at least at intervals;

measuring the rate of change of sensed pressure over a period of at least 10 seconds; and generating an alarm signal if the rate of charge of pressure during said period exceeds a predetermined amount.

* * * * *